United States Patent
Weyl et al.

(10) Patent No.: US 6,878,252 B2
(45) Date of Patent: Apr. 12, 2005

(54) GAS SENSOR

(75) Inventors: Helmut Weyl, Schwieberdingen (DE); Juergen Wilde, Fellbach (DE)

(73) Assignee: Robert Bosch GmbH, Stuttgart (DE)

( * ) Notice: Subject to any disclaimer, the term of this patent is extended or adjusted under 35 U.S.C. 154(b) by 96 days.

(21) Appl. No.: 10/191,182

(22) Filed: Jul. 8, 2002

(65) Prior Publication Data
US 2003/0019751 A1 Jan. 30, 2003

(30) Foreign Application Priority Data
Jul. 6, 2001 (DE) ......................................... 101 32 828

(51) Int. Cl.[7] .......................................... G01N 27/407
(52) U.S. Cl. ...................... 204/424; 204/428; 29/592.1
(58) Field of Search ................................ 204/421–429; 29/592.1

(56) References Cited

U.S. PATENT DOCUMENTS

| | | | | |
|---|---|---|---|---|
| 4,400,258 A | * | 8/1983 | Hans-Jurgen et al. | |
| 4,425,918 A | * | 1/1984 | Moll et al. | |
| 5,246,562 A | * | 9/1993 | Weyl et al. | |
| 5,711,863 A | * | 1/1998 | Henkelmann et al. | |
| 5,942,092 A | * | 8/1999 | Weyl et al. | |
| 6,083,371 A | * | 7/2000 | Weyl et al. | |
| 6,164,120 A | * | 12/2000 | Friese et al. | |

FOREIGN PATENT DOCUMENTS

EP 0 506 897 5/1992

* cited by examiner

*Primary Examiner*—Kaj K. Olsen
(74) *Attorney, Agent, or Firm*—Kenyon & Kenyon

(57) ABSTRACT

A gas sensor is provided, for example, a sensor for determining the concentration or the temperature of a gas component. The gas sensor has a housing, in which a sensor element having at least one contact surface is arranged. The contact surface is conductively connected to a conductor element. The sensor element having the contact surface and the conductor element is arranged between two contact supports situated opposite one another. A spring element contacting the contact supports presses the conductor element onto the contact surface. Each of the contact supports, on sides facing one another, has at least one recess and at least one protuberance, the protuberance of one contact support engaging in the recess of the other contact support, and vice versa.

20 Claims, 4 Drawing Sheets

GAS SENSOR

FIELD OF THE INVENTION

The present invention relates to a gas sensor.

BACKGROUND INFORMATION

A known gas sensor is referred to, for example, in European Published Patent Application No. 0 506 897 for use in analyzing the exhaust gas of internal combustion engines. Gas sensors of this type may include a metallic housing, in which an elongated, planar sensor element having a measuring-side and a connection-side area is disposed in an electrically insulated manner. The sensor element may have contact surfaces in the connection-side area, which are electrically connected to a measuring point located in the measuring-side area. The gas sensor may also have a contacting arrangement, which contains conductor elements conductively connected to the contact surfaces and emerging from the housing. The conductor elements are pressed onto the contact surfaces by a spring element, which acts upon two contact supports opposite one another.

In this context, it is believed to be disadvantageous of the above-described gas sensor that the contact supports may rotate with respect to one another, for example, during assembly. As a result, the contacting of the sensor element may be defective.

SUMMARY OF THE INVENTION

An exemplary gas sensor according to the present invention advantageously includes a securely fixed contacting arrangement. For this purpose, the contacting arrangement has at least two contact supports, one of which has at least one protuberance on the side facing the other contact support, the protuberance engaging in a corresponding recess of the other contact support.

As a result, the contact supports may be securely fixed with respect to one another, thus preventing the contact supports from slipping or rotating with respect to one another, for example, during assembly or when installed in the gas sensor.

It is believed that a secure mounting is assured, or at least made more probable, if the protuberances and/or recesses of the contact supports are shaped as a hemisphere, pyramid, or semi-cylinder, and if the protuberance of the one contact support at least approximately completely fills the corresponding recess of the other contact support.

If every contact support includes two protuberances, one protuberance and one recess, or two recesses, respectively, which interlock in corresponding protuberances and/or recesses of every opposite contact support, the contact supports may be prevented from rotating with respect to one another, even when hemispherical protuberances and recesses are provided.

Production may be simplified if contact supports facing each other have the same shape. For this purpose, the protuberance and recess of one contact support may be arranged in a plane that is perpendicular to the longitudinal axis of the sensor element. In exemplary protuberances and/or recesses according to the present invention, the contact supports may tilt during assembly in a defined manner, thus simplifying the assembly process. In this way, the protuberances and recesses may function as an articulated joint.

DETAILED DESCRIPTION

Figure 1:
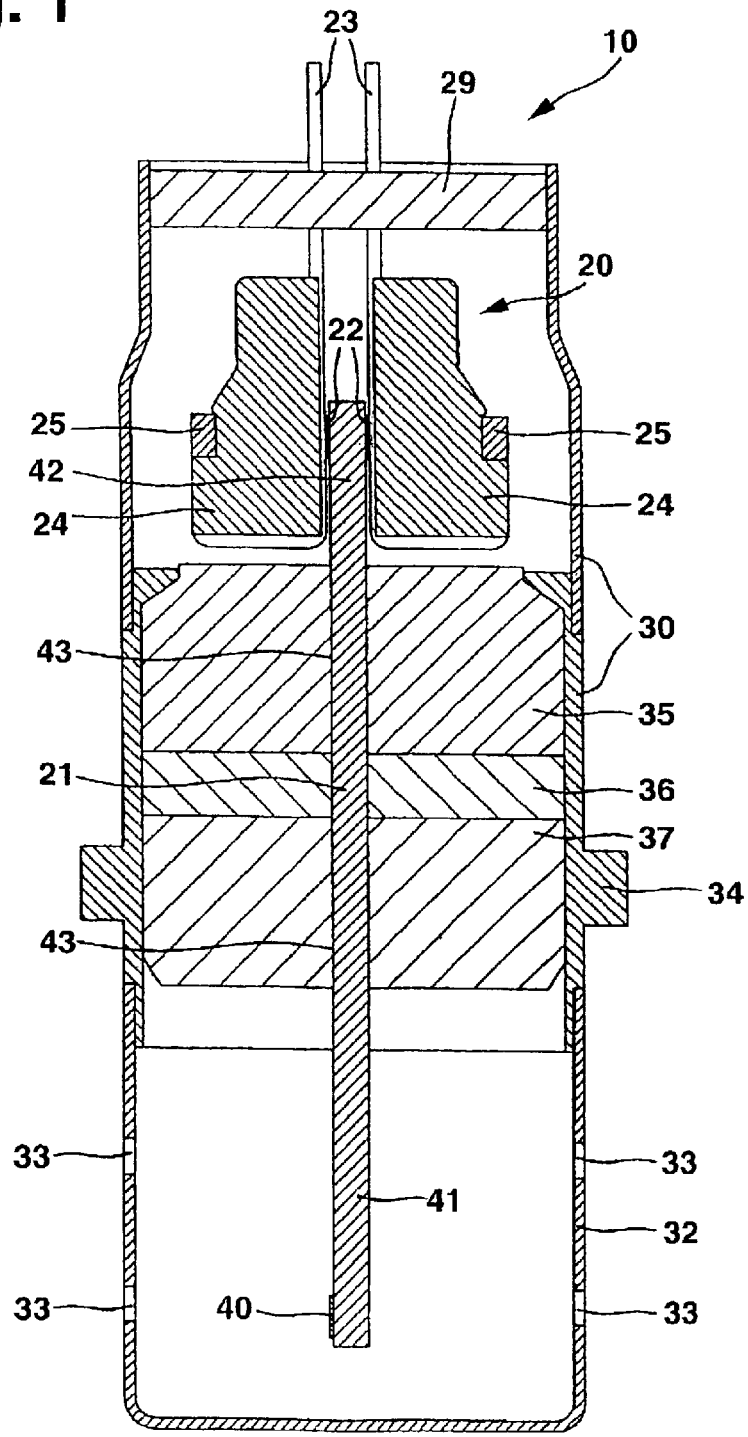
FIG. 1 is a cross section of a gas sensor having a contacting arrangement.

FIG. 1 is a cross section of a gas sensor 10 having a metallic housing 30, in which a connection-side and a measuring-gas-side ceramic molded part 35, 37 are disposed. Both ceramic molded parts 35, 37 have through openings 43, extending in alignment with one another, in which is located a plate-shaped sensor element 21 having a measuring-gas-side end segment 41 and a connection-side end segment 42. A sealing element 36 is arranged between connection-side and measuring-gas-side ceramic molded parts 35, 37.

Measuring-gas-side end segment 41 of sensor element 21 protrudes out of housing 30 and is surrounded by a protective tube 32, which is secured to housing 30. Gas sensor 10 may be mounted in a measuring opening of a measuring gas chamber (not shown), for example, of an exhaust gas line of an internal combustion engine, using a collar 34. The gas to be measured reaches a measuring point 40 located on measuring-gas-side end segment 41 of sensor element 21 through intake and outlet openings 33 of protective tube 32.

Connection-side end segment 42 of sensor element 21 has contact surfaces 22, for which a contacting arrangement 20 having conductor elements 23, contact supports 24, and a spring element 25 is provided. Conductor elements 23 emerge from housing 30 in a connecting line (not shown), which is connected to evaluation electronics (not shown). Housing 30 terminates on the connection side in a disk 29, which has openings for conductor elements 23.

FIGS. 2 through 10 show exemplary gas sensors according to the present invention, which are different from the gas sensor described with reference to FIG. 1 in the configuration of the contacting arrangement.

Figure 2:
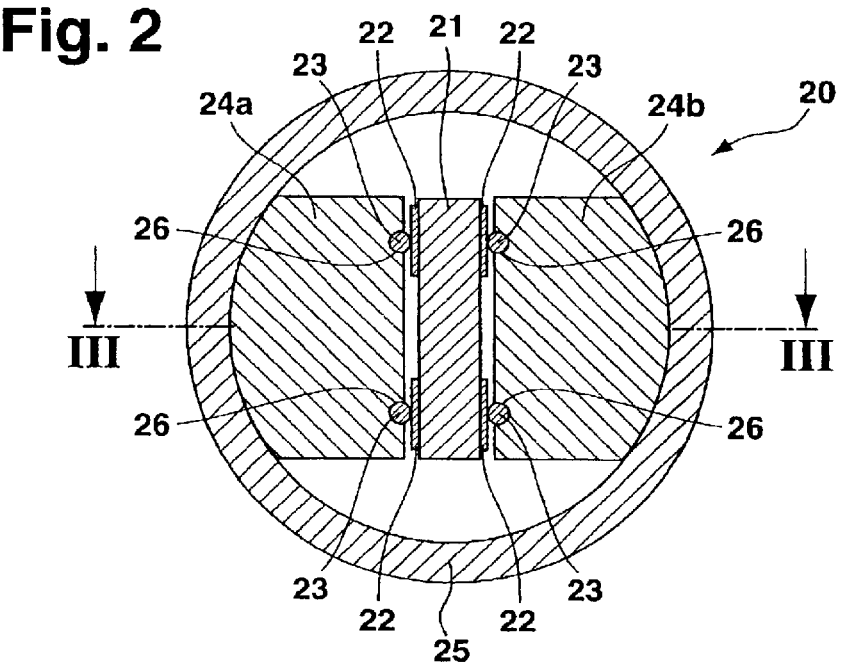
FIG. 2 is a sectional view of a first exemplary contacting arrangement according to the present invention along line II—II of FIG. 3.
Figure 3:
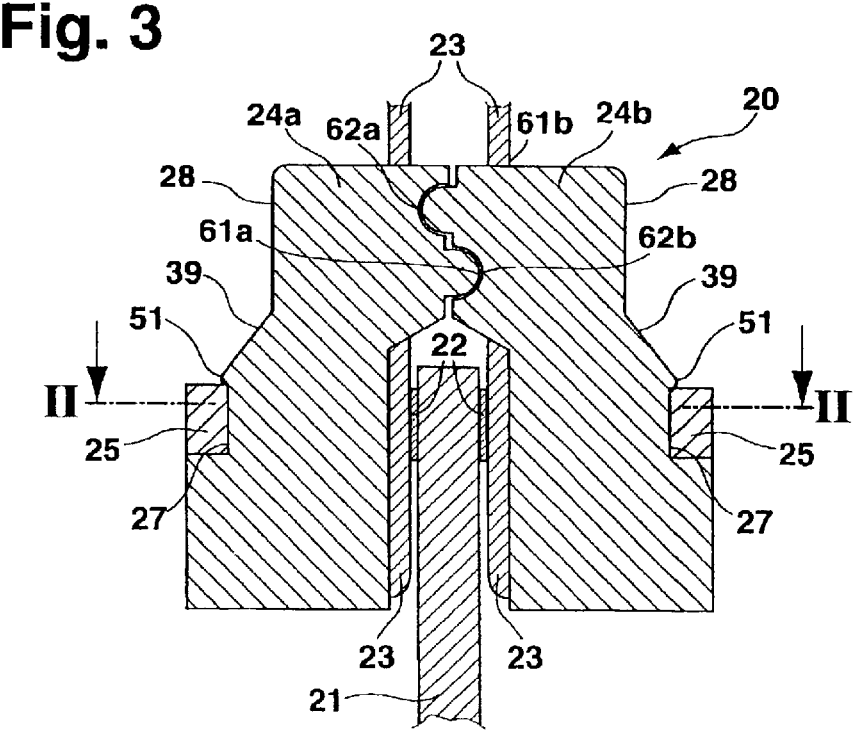
FIG. 3 is a sectional view of the first exemplary contacting arrangement according to the present invention along line III—III of FIG. 2.

FIGS. 2 and 3 show the area of the contacting arrangement of a first exemplary embodiment according to the present invention. In this context, corresponding elements are designated by the same reference numerals as in FIG. 1. Connection-side end segment 42 of sensor element 21 has four contact surfaces 22, two of which are arranged on each of two large surfaces of sensor element 21 facing the outside. Two recesses 26 are arranged on each side of two contact supports 24a, 24b of contacting arrangement 20 facing sensor element 21, conductor elements 23 being arranged in the two recesses 26. Conductor elements 23 contact corresponding contact surfaces 22 of sensor element 21 via the part protruding from recesses 26. Spring element 25, which acts upon contact supports 24a, 24b, presses conductor elements 23 onto contact surfaces 22.

Recess 26 of contact support 24a, 24b are provided on the side of sensor element 21 facing contact surfaces 22 and around contact support 24a, 24b on the side facing the measuring-gas chamber and, at least in certain areas, on the side facing away from contact surfaces 22 of sensor element 21. Conductor element 23 extends within recess 26, and an appropriate hook-shaped formation secures conductor element 23 on contact support 24a, 24b.

Spring element 25 is arranged in a locking step 27 of both contact supports 24a, 24b and presses conductor elements 23 onto respective contact surfaces 22 of sensor element 21 via contact supports 24a, 24b. Locking step 27 is arranged at the level of contact surfaces 22. Thus, contact surfaces 22 are arranged at least partially in the interior of annular spring element 25, which is situated in locking step 27. Contact supports 24a, 24b have a further locking step 28, in which spring element 25 is supported with no prestressing or with less prestressing than in locking step 27. From further locking step 28, spring element 25 may be pushed onto locking step 27 over an inclined area 39 and a locking protuberance 51.

Each of contact supports 24a, 24b has a protuberance 61a, 61b and recess 62a, 62b, protuberance 61a of one contact support 24a interlocking in recess 62b of the other contact support 24b in the assembled state. Conversely, recess 62a of one contact support 24a base is filled by protuberance 61b of the other contact support 24b. Thus, protuberance 61a, 61b at least approximately fills corresponding recess 62a, 62b.

FIGS. 4 through 10 show a second exemplary embodiment of the present invention, which includes a configuration of contact support 124 and of spring element 125 that is different from the first exemplary embodiment.

Figure 10:
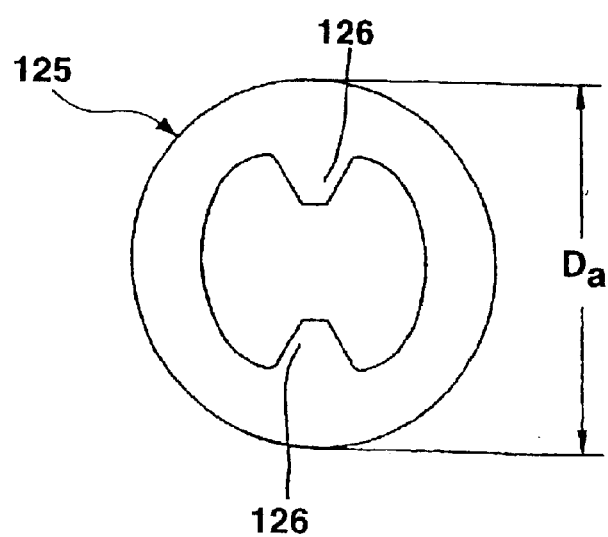
FIG. 10 shows a spring element of the second exemplary gas sensor according to the present invention.

Spring element 125 of FIG. 10 is a stamped disk part, which is closed in annular fashion, having an essentially H-shaped opening in cross-section, and having two tongues 126 directed to the inside. If spring element 125 is pushed over contact support 124, tongues 126 bend back opposite the slide-on direction. Simultaneously, disk-shaped spring element 125 bends, the concave side of the curved disk being oriented in the slide-on direction.

Figure 4:
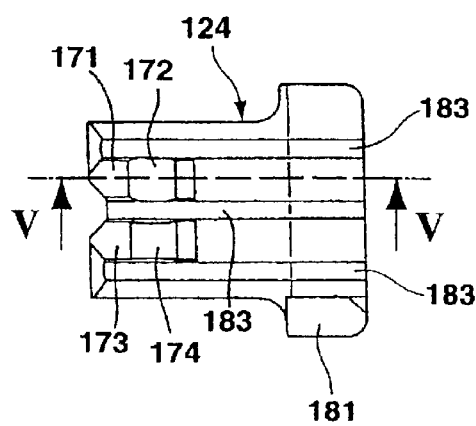
FIGS. 4 through 9 are various views of a contact support of a second exemplary gas sensor according to the present invention.
Figure 5:
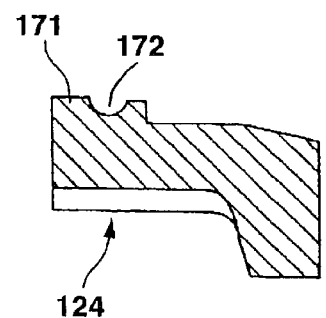
Figure 6:
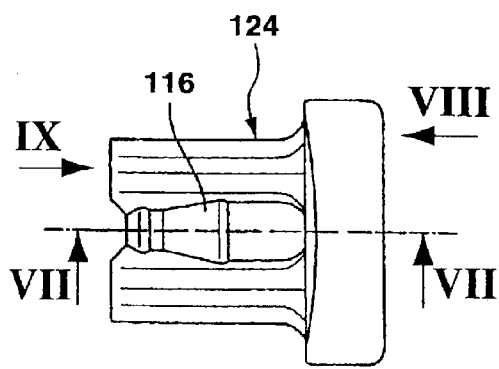
Figure 8:
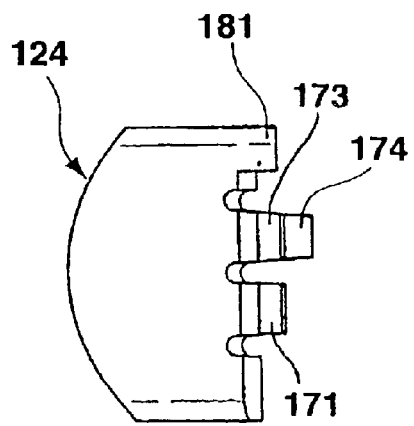
Figure 9:
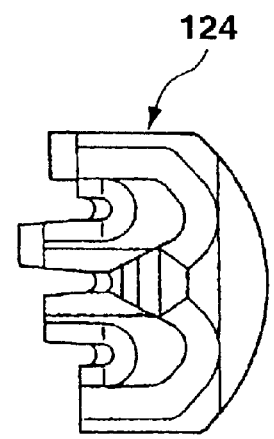

FIG. 4 shows the side of contact support 124 facing sensor element 21 to be supported (not shown). The opposite side of contact support 124 is shown in FIG. 6. FIGS. 8 and 9 show the two end faces of contact support 124, and FIGS. 5 and 7 show sectional views along lines V—V of FIG. 4 and VII—VII of FIG. 6, respectively.

Figure 7:
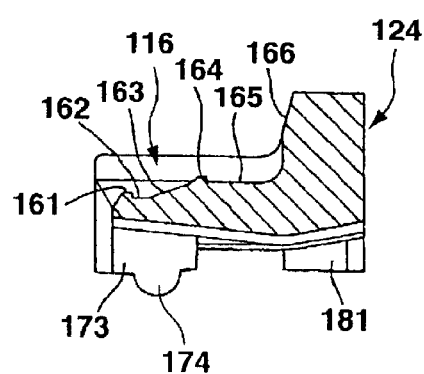

As shown in FIGS. 6 and 7, contact support 124 has an axial furrow 116 on its exterior side, into which spring element 125 engages via one of tongues 126. The base of furrow 116, on the left end of contact support 124 of FIGS. 6 and 7, has a first locking protuberance 161, which is adjacent to a first locking step 162 to the right. The latter towards the right passes over into an inclined area 163, which is adjacent to a second locking protuberance 164 and a second locking step 165, situated behind the former.

Therefore, if spring element 125 of FIG. 10 is pushed onto first locking step 162, tongues 126 extending beyond first locking protuberance 161, spring element 125 adopts a first locking position. In response to a further pushing to the right of spring element 125 of FIGS. 6 and 7, tongues 126, in response to the increasing bending of tongues 126 and of entire spring element 125, are placed in a biased second locking position passing over inclined area 163 and second locking protuberance 164, tongues 126 in second locking position being biased against second locking step 165, and annular, disk-shaped spring element 125 contacting a limit stop surface 166 of contact support 124.

As shown in FIGS. 4 through 9, one specific feature of contact support 124 is that the contact support, together with an identical contact support 124, forms a mouth, which may be suitable for receiving sensor element 21, the mouth being capable of gripping the sensor element 21 in a pincer-like fashion.

For this purpose, as shown in FIGS. 4, 5, and 7, contact support 124 has a projection 171 at its left end. The projection 171 has a recess 172, which is at least roughly semi-circular in cross-section, and has a further projection 173, which includes a protuberance 174 corresponding to recess 172.

In the two-by-two arrangement of contact support 124 shown in FIGS. 4 through 9, recess 172 of the one pressure element accommodates protuberance 174 of the other pressure element, and vice versa. Projections 171 and 173, having recesses 172 and protuberances 174, respectively, therefore form a "jaw hinge," which is held together by spring element 125, if tongues 126 rest on the locking surfaces of first locking step 162, as shown in FIG. 10.

As shown in FIGS. 4, 7, 8, and 9, a lateral projection 181 is arranged on the right end of contact support 124. Therefore, if two contact supports 124 are arranged in pairs, creating the aforementioned jaw hinge, lateral projection 181 of each contact support 124 is directed at an opposite planar area on the other contact support 124 that does not have a projection.

Projections 171, 173, 181, and recesses 172 and protuberances 174 are configured so that contact supports 124 tilt with respect to one another, in response to a displacement of spring element 125 from first locking step 162 into second locking step 165. If spring element 125 is in first locking step 162, the distance between the two contact supports 124 on the side facing sensor element 21 permits sensor element 21 to be pushed between contact supports 124 and conductor elements 23 arranged in conductor element recesses 183. If spring element 125 is pushed into second locking step 165, conductor elements 23 are pressed against contact surfaces 22 of sensor element 21, as a result of the tilting motion of contact supports 124. In these tilting motions, recesses 172 and protuberances 174, which interlock in one another, function as a ball-and-socket joint.

In another exemplary embodiment according to the present invention, the contact supports may have pin-shaped or block-shaped protuberances and/or recesses, which may aid, for example, in fixing the contact supports with respect to one another. These protuberances and recesses may be laterally arranged next to protuberances 61a, 61b, 174 and recesses 62a, 62b, 172, which, on account of their shapes, permit a tilting motion of contact supports 24a, 24b, 124 and which may function, for example, as a lateral guide for the tilting motion and as a further fixing of the contact supports with respect to one another.

What is claimed is:

1. A gas sensor, comprising:
    a housing;
    a conductor element;
    a sensor element arranged in the housing, the sensor element having at least one contact surface conductively connected to the conductor element;
    first and second contact supports arranged opposite one another, one of the first and second contact supports including at least one protuberance engaging in at least one recess of the other one of the first and second contact supports, the sensor element and the conductor element being arranged between the first and second contact supports; and
    at least one spring element contacting at least one of the first and second contact supports, the at least one spring element pressing the conductor element onto the at least one contact surface of the sensor element;
    wherein the first and second contact supports each having a first end face and an opposite second end face from which the sensor element projects, the at least one protuberance and the recess lying between the at least one contact surface and each first end face.

2. The gas sensor according to claim 1, wherein the gas sensor is operable to determine one of a concentration and a temperature of a gas component.

3. The gas sensor according to claim 1, wherein each of the first and second contact supports includes at least one recess and at least one protuberance on a side facing the other one of the first and second contact supports, the at least one protuberance of each of the first and second contact supports engaging in the at least one recess of the other one of the first and second contact supports.

4. The gas sensor according to claim 3, wherein the at least one protuberance and the at least one recess are arranged in a plane that is perpendicular to a longitudinal axis of the sensor element.

5. The gas sensor according to claim 3, wherein the at least one protuberance and the at least one recess interlock one another, so that the first and second contact supports tilt with respect to one another.

6. The gas sensor according to claim 1, wherein the first contact support includes at least two protuberances and the second contact support includes at least two recesses, the at least two protuberances of the first contact support engaging in the at least two recesses of the second contact support.

7. The gas sensor according to claim 1, wherein each of the at least one protuberance and the at least one recess has one of a hemispherical shape, a pyramidal shape, a semi-cylindrical shape, a pin shape, and a block shape.

8. The gas sensor according to claim 7, wherein a selected one of the first and second contact supports includes at least one additional lateral protuberance having one of a pin-shape and a block-shape, the at least one additional protuberance being arranged adjacent to one of the at least one protuberance and the at least one recess of the selected one of the first and second contact supports, the at least one additional protuberance engaging in at least one corresponding recess of the other one of the first and second contact supports, the at least one corresponding recess having one of a pin-shape and a block-shape.

9. The gas sensor according to claim 1, wherein the at least one protuberance at least approximately fills the at least one recess.

10. The gas sensor according to claim 1, wherein the gas sensor is operable to determine one of a concentration and a temperature of a gas component, and each of the first and second contact supports includes at least one recess and at least one protuberance on a side facing the other one of the first and second contact supports, the at least one protuberance of each of the first and second contact supports engaging in the at least one recess of the other one of the first and second contact supports.

11. The gas sensor according to claim 10, wherein each of the at least one protuberance and the at least one recess has one of a hemispherical shape, a pyramidal shape, a semi-cylindrical shape, a pin shape, and a block shape.

12. The gas sensor according to claim 11, wherein a selected one of the first and second contact supports includes at least one additional lateral protuberance having one of a pin-shape and a block-shape, the at least one additional protuberance being arranged adjacent to one of the at least one protuberance and the at least one recess of the selected one of the first and second contact supports, the at least one additional protuberance engaging in at least one corresponding recess of the other one of the first and second contact supports, the at least one corresponding recess having one of a pin-shape and a block-shape.

13. The gas sensor according to claim 1, wherein the gas sensor is operable to determine one of a concentration and a temperature of a gas component, and the first contact support includes at least two protuberances and the second contact support includes at least two recesses, the at least two protuberances of the first contact support engaging in the at least two recesses of the second contact support.

14. The gas sensor according to claim 13, wherein each of the at least one protuberance and the at least one recess has one of a hemispherical shape, a pyramidal shape, a semi-cylindrical shape, a pin shape, and a block shape.

15. The gas sensor according to claim 14, wherein a selected one of the first and second contact supports includes at least one additional lateral protuberance having one of a pin-shape and a block-shape, the at least one additional protuberance being arranged adjacent to one of the at least one protuberance and the at least one recess of the selected one of the first and second contact supports, the at least one additional protuberance engaging in at least one corresponding recess of the other one of the first and second contact supports, the at least one corresponding recess having one of a pin-shape and a block-shape.

16. A method for producing a gas sensor, comprising the steps of:
    placing first and second contact supports and at least one conductor element onto a sensor element, the first and second contact supports being arranged opposite one another;
    arranging a spring element on a first locking step, the spring element clamping the first and second contact supports to at least one another and the sensor element;
    pushing the spring element over an inclined area onto a second locking step, thereby reducing a distance between the first and second contact supports in an area of contact surfaces of the sensor element by a tilting motion of the first and second contact supports; and
    pressing the at least one conductor element onto the contact surfaces of the sensor element;
    wherein interlocking recesses and protuberances of the first and second contact supports form an articulated joint for the tilting motion.

17. The method according to claim 16, wherein the protuberances and the recesses are one of hemispherically shaped and semi-cylindrically shaped, and wherein the first and second contact supports have identical shapes.

18. A gas sensor, comprising:
    a housing;
    a conductor element;
    a sensor element arranged in the housing, the sensor element having at least one contact surface conductively connected to the conductor element;
    first and second contact supports arranged opposite one another and configured to be pivotal relative to one another along a longitudinal axis of the housing and the first and second contact supports, the sensor element and the conductor element being arranged between the first and second contact supports; and
    at least one spring element contacting at least one of the first and second contact supports, the at least one spring element pressing the conductor element onto the at least one contact surface of the sensor element.

19. The gas sensor according to claim 18, wherein one of the first and second contact supports include at least one protuberance engaging in at least one recess of the other one of the first and second contact supports.

20. The gas sensor according to claim 19, wherein the first and second contact supports each have a first end face and an opposite second end face from which the sensor element projects, the at least one protuberance and the recess lye between the at least one contact surface and each first end face.

* * * * *